United States Patent
Yu et al.

(10) Patent No.: US 11,525,009 B2
(45) Date of Patent: Dec. 13, 2022

(54) BISPECIFIC ANTIBODY AND ANTIBODY CONJUGATE FOR TUMOR THERAPY AND USE THEREOF

(71) Applicant: BENHEALTH BIOPHARMACEUTIC (SHENZHEN) CO. LTD., Shenzhen (CN)

(72) Inventors: Haoyang Yu, Shenzhen (CN); Zhong Wang, Shenzhen (CN); Zhengcheng Li, Shenzhen (CN)

(73) Assignee: BENHEALTH BIOPHARMACEUTIC (SHENZHEN) CO. LTD., Shenzhen (CN)

( * ) Notice: Subject to any disclaimer, the term of this patent is extended or adjusted under 35 U.S.C. 154(b) by 882 days.

(21) Appl. No.: 16/312,100

(22) PCT Filed: Jun. 21, 2017

(86) PCT No.: PCT/CN2017/089307
§ 371 (c)(1),
(2) Date: Dec. 20, 2018

(87) PCT Pub. No.: WO2017/219974
PCT Pub. Date: Dec. 28, 2017

(65) Prior Publication Data
US 2019/0276554 A1    Sep. 12, 2019

(30) Foreign Application Priority Data

Jun. 22, 2016 (CN) .......................... 201610456791.8
Jan. 24, 2017 (CN) .......................... 201710052692.8

(51) Int. Cl.
| | |
|---|---|
| *A61K 39/395* | (2006.01) |
| *C07K 16/30* | (2006.01) |
| *A61K 47/59* | (2017.01) |
| *A61K 47/69* | (2017.01) |
| *A61K 47/65* | (2017.01) |
| *A61K 47/68* | (2017.01) |
| *A61P 35/00* | (2006.01) |
| *A61K 35/17* | (2015.01) |
| *C07K 16/28* | (2006.01) |
| *C07K 16/46* | (2006.01) |
| *C12N 15/85* | (2006.01) |
| *C07K 17/08* | (2006.01) |

(52) U.S. Cl.
CPC .......... *C07K 16/3092* (2013.01); *A61K 35/17* (2013.01); *A61K 39/395* (2013.01); *A61K 47/593* (2017.08); *A61K 47/65* (2017.08); *A61K 47/6883* (2017.08); *A61K 47/6937* (2017.08); *A61P 35/00* (2018.01); *C07K 16/28* (2013.01); *C07K 16/283* (2013.01); *C07K 16/46* (2013.01); *C07K 17/08* (2013.01); *C12N 15/85* (2013.01)

(58) Field of Classification Search
CPC ............ A61K 39/395; A61K 39/39558; C07K 16/283; C07K 16/468; C07K 16/30
USPC .......................................... 424/133.1, 136.1
See application file for complete search history.

(56) References Cited

U.S. PATENT DOCUMENTS

| | | | |
|---|---|---|---|
| 10,758,625 B2 | 9/2020 | Yu et al. | |
| 11,000,603 B2 | 5/2021 | Yu et al. | |
| 2004/0219203 A1 | 11/2004 | Griffiths et al. | |
| 2004/0219224 A1 | 11/2004 | Yakovlevsky et al. | |
| 2010/0266496 A1 | 10/2010 | Hansen et al. | |
| 2015/0010567 A1 | 1/2015 | Bourquin et al. | |
| 2015/0377869 A1 | 12/2015 | Berkelman et al. | |
| 2021/0395387 A9* | 12/2021 | Yu ........................... | A61P 37/02 |

FOREIGN PATENT DOCUMENTS

| | | |
|---|---|---|
| CN | 104271602 | 1/2015 |
| CN | 104829730 | 8/2015 |
| WO | 03048209 | 6/2003 |
| WO | 2004110390 | 12/2004 |
| WO | 2005103081 | 11/2005 |
| WO | 2006079120 | 7/2006 |
| WO | 2006094192 | 9/2006 |
| WO | 2007047609 | 4/2007 |
| WO | 2013090293 | 6/2013 |
| WO | 2014047231 | 3/2014 |
| WO | 2014079000 | 5/2014 |
| WO | 2014/110591 A1 | 7/2014 |
| WO | 2014153002 | 9/2014 |
| WO | 2015095412 | 6/2015 |
| WO | 2016/165301 A1 | 10/2016 |
| WO | 2016/165302 A1 | 10/2016 |
| WO | 2016165632 | 10/2016 |

(Continued)

OTHER PUBLICATIONS

Li et al. (PLoS ONE 13(1): e019102 (Jan. 22, 2018)).*

(Continued)

*Primary Examiner* — Lynn A Bristol

(57) ABSTRACT

Provided in the present invention is a bispecific antibody which comprises an anti-MUC1 VHH antibody fragment and an anti-CD16 VHH antibody fragment. The antibody fragment used in the present invention is a variable region sequence derived from a heavy chain camelid antibody and has a high binding affinity to the antigen. Antibody fragments recognizing MUC1 and CD16 are constructed in the same antibody molecule by the invention, so that the antibody molecule can specifically bind to MUC1 and CD16 molecules to promote the killing effect of NK cells on MUC1-positive expression cells and has an inhibiting effect on the growth of MUC1-positive tumors. Also provided is a conjugate of the bispecific antibodies, a related pharmaceutical composition and use.

Figure 1:
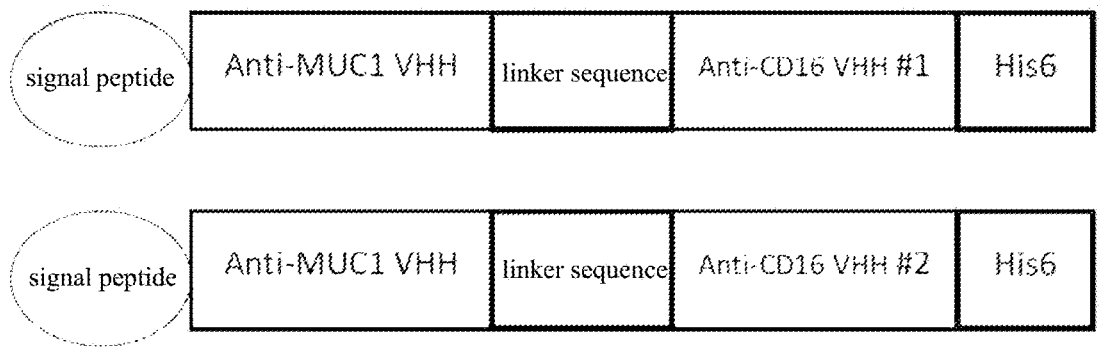

17 Claims, 5 Drawing Sheets
Specification includes a Sequence Listing.

(56) References Cited

FOREIGN PATENT DOCUMENTS

| WO | 2017185662 | 11/2017 |
|---|---|---|
| WO | 2017219974 | 12/2017 |

OTHER PUBLICATIONS

Database Caplus Chemical Abstracts Service, Columbus, OH, US; Registry No. 1905409-39-3, Mosunetuzumab, Entered May 6, 2016 (Registry No. 1905409-39-3).
Sun, et al. "Anti-CD20/CD3 T cell-dependent bispecific antibody for the treatment of B cell malignancies." Science translational medicine 7, No. 287 (2015): 287ra70-287ra70.
Summons to Oral Proceedings European Application No. 16779607.7, mailed May 12, 2021, 14 pages.
Steenblock et al. A comprehensive platform for ex vivo T-cell expansion based on biodegradable polymeric artificial antigen-presenting cells. Molecular Therapy. Apr. 1, 2008;16(4):765-72.
European Application No. 18744269.4, Extended European Search Report dated May 10, 2021, 16 pages.
Cheng et al., Magnetic Antibody-Linked Nanomatchmakers for Therapeutic Cell Targeting, Nature Communications, vol. 4880, No. 5, Sep. 10, 2014, 9 pages.
Danielczyk, et al., PankoMab: A Potent New Generation Anti-Tumour MUC1 Antibody, Cancer Immunol Immunother, vol. 55, No. 11, Nov. 2006, pp. 1337-1347.
Dominguez et al., Targeting the Tumor Microenvironment with Anti-Neu/Anti-CD40 Conjugated Nanoparticles for the Induction of Antitumor Immune Responses, Vaccine, vol. 28, No. 5, Feb. 3, 2010, pp. 1383-1390.
Dong, et al., A Novel Bispecific Antibody, BiSS, with Potent Anti-Cancer Activities Cancer Biology and Therapy, vol. 17, No. 4, Apr. 2, 2016, pp. 364-370.
European Application No. 16779607.7, Partial Supplemental European Search Report dated Aug. 13, 2018, 18 pages.
European Application No. 16900170.8, Extended European Search Report dated Nov. 26, 2019, 10 pages.
European Application No. 17814712.0, Extended European Search Report dated Jan. 13, 2020, 7 pages.
Fiedler, et al., A Phase I Study of Pankomab-GEX, A Humanised Glyco-Optimised Monoclonal Antibody to a Novel Tumour-Specific MUC1 Glycopeptide Epitope in Patients with Advanced Carcinomas, European Journal of Cancer, vol. 63, Aug. 2016, pp. 55-63.
Glorius et al., The Novel Tribody [(CD20)2XCD16] Efficiently Triggers Effector Cell-mediated Lysis of Malignant B Cells, Leukemia, vol. 27, No. 1, Jun. 4, 2012, pp. 190-201.
Katayose et al., MUC1-Specific Targeting Immunotherapy With Bispecific Antibodies: Inhibition of Xenografted Human Bile Duct Carcinoma Growth, Cancer Research, vol. 56, No. 18, Sep. 15, 1996, pp. 4205-4212.
Kellner et al., Heterodimeric Bispecific Antibody-derivatives Against CD19 and CD16 Induce Effective Antibody-Dependent Cellular Cytotoxicity Against B-lymphoid Tumor Cells, Cancer Letters, vol. 303, No. 2, Apr. 28, 2011, pp. 128-139.
Kodama et al., Mutated SEA-D227a-Conjugated Antibodies Greatly Enhance Antitumor Activity Against MUC1-Expressing Bile Duct Carcinoma, Cancer Immunology, Immunotherapy, vol. 50, Dec. 2001, pp. 539-548.
Mahapatro et al., Biodegradable Nanoparticles are Excellent Vehicle for Site Directed In-Vivo Delivery of Drugs and Vaccines, Journal of Nanobiotechnology, vol. 9, No. 1, Jan. 1, 2011, 11 pages.
International Application No. PCT/CN2016/079307, International Search Report and Written Opinion dated Jul. 21, 2016, 21 pages.
International Application No. PCT/CN2016/101984, International Search Report and Written Opinion dated Feb. 4, 2017, 26 pages.
International Application No. PCT/CN2018/073785, International Preliminary Report on Patentability dated Jul. 30, 2019, 12 pages.
International Application No. PCT/CN2018/073785, International Search Report and Written Opinion dated Apr. 12, 2018, 18 pages.
Sadeqzadeh, et al., Combined MUC1-Specific Nanobody-Tagged PEG-Polyethylenimine Polyplex Targeting and Transcriptional Targeting of tBid Transgene for Directed Killing of MUC1 Over-Expressing Tumour Cells, Journal of Controlled Release, vol. 156, No. 1, Nov. 30, 2011,pp. 85-91.
Schlenzka et al., Combined Effect of Recombinant CD19×CD16 Diabody and Thalidomide in a Preclinical Model of Human B Cell Lymphoma, Anti-Cancer Drugs, vol. 15, No. 9, Oct. 2004, pp. 915-919.
Takemura et al., A Mutated Superantigen SEA D227A Fusion Diabody Specific to MUC1 and CD3 in Targeted Cancer Immunotherapy for Bile Duct Carcinoma, Cancer Immunology, Immunotherapy, vol. 51, No. 1, Mar. 1, 2002, pp. 33-44.
Tang et al., Bispecific Antibodies, Nanoparticles and Cells: Bringing the Right Cells to Get the Job Done, Expert Opin. Biol. Ther., vol. 15, No. 9, 2015, pp. 1251-1255.
Wei, et al., Human MUC1 Oncoprotein Regulates p53-Responsive Gene Transcription in the Genotoxic Stress Response, Cancer Cell, vol. 7, No. 2, Feb. 1, 2005, pp. 167-178.
Yeheskely-Hayon et al., Optically Induced Cell Fusion Using Bispecific Nanoparticles, Small, vol. 9, No. 22, Nov. 25, 2013, pp. 3771-3777.
Zhengcheng et al., Production and Function Evaluation of a Kind of Bispecific Antibody Crosslinked with PLGA Nanoparticles in Vitro, Immunological Journal, vol. 32, No. 1, Jan. 2016, pp. 34-37.
Zhi et al., Cytotoxicity of Cytokine-Induced Killer Cells Targeted by the Bispecific Antibody Anti-CD3xanti-AFP on AFP Positive Hepatoma Cells, Chinese Journal of Biochemical Pharmaceutics, Chinese Journal of Biochemical Pharmaceutics, No. 5, May 31, 2010, pp. 297-301.
Bryant et al., Magnetic Needles and Superparamagnetic Cells, Physics In Medicine and Biology, Institute of Physics Publishing, vol. 52, No. 14, Jul. 21, 2007, pp. 4009-4025.
European Application No. EP18744269.4, Partial Supplemental European Search Report, dated Dec. 18, 2020, 16 pages.
Taylor et al., Nanocell Targeting Using Engineered Bispecific Antibodies, MABS, vol. 7, No. 1, Dec. 18, 2014, 14 pages.
Wild et al., Tumor Therapy with Bispecific Antibody: The Targeting and Triggering Steps can be Separated Employing a Cd2-Based Strategy, The Journal of Immunology, vol. 163, No. 4, Aug. 15, 1999, 9 pages.
Wu et al., Bispecific Antibody Conjugated Manganese-Based Magnetic Engineered Iron Oxide for Imaging of HER2/neu- and EGFR-Expressing Tumors, Theranostics, vol. 6, No. 1, 2016, pp. 118-130.
European Application No. 17814712.0, Intention to Grant dated Jun. 9, 2021, 7 pages.
U.S. Appl. No. 16/130,031, Final Office Action dated Nov. 20, 2020, 10 pages.
Arruebo et al., Antibody-Conjugated Nanoparticles for Biomedical Applications, Journal of Nanomaterials, vol. 2009, Article ID 439389, 2009, 24 pages.
European Application No. EP16779607.7, Office Action dated Sep. 15, 2020, 6 pages.
Lchiyama et al., Karei Igaku Kenkyusho Zasshi, vol. 51, No. 3-4, 2000, pp. 111-120.
Prasad et al., Optimization of Stability, Encapsulation, Release, and Cross-Priming of Tumor Antigen-Containing PLGA Nanoparticles, Pharmaceutical Research, vol. 29, No. 9, Sep. 2012, pp. 2565-2577.
Yu et al., A Novel Approach of Targeted Immunotherapy against Adenocarcinoma Cells with Nanoparticles Modified by CD16 and MUC1 Aptamers, Journal of Nanomaterials, Article ID 316968, vol. 2015, Oct. 2015, 11 pages.
U.S. Appl. No. 16/130,031, Notice of Allowance dated Feb. 5, 2021, 8 pages.
U.S. Appl. No. 16/935,679, Non-Final Office Action dated Mar. 3, 2021, 19 pages.
European Application No. 16900170.8, Office Action dated Feb. 5, 2021, 6 pages.
U.S. Appl. No. 15/548,630, Non-Final Office Action, dated Nov. 19, 2019, 22 pages.
U.S. Appl. No. 15/548,630, Notice of Allowance, dated Apr. 29, 2020, 11 pages.
U.S. Appl. No. 16/130,031, Non-Final Office Action, dated Aug. 13, 2020, 25 pages.

(56) References Cited

OTHER PUBLICATIONS

International Search Report and Written Opinion issued for Application No. PCT/CN2017/089307 dated Sep. 26, 2017, along with an English translation.

* cited by examiner

SEQUENCE LISTING

<160> NUMBER OF SEQ ID NOS: 4

<210> SEQ ID NO 1
<211> LENGTH: 119
<212> TYPE: PRT
<213> ORGANISM: Artificial sequence
<220> FEATURE:
<223> OTHER INFORMATION: Synthetic construct

<400> SEQUENCE: 1

```
Glu Val Gln Leu Gln Glu Ser Gly Gly Gly Ser Val Gln Thr Gly Gly
1               5                   10                  15

Ser Leu Arg Leu Ser Cys Val Val Ser Gly Tyr Thr Tyr Ser Ser Ala
            20                  25                  30

Cys Met Gly Trp Phe Arg Gln Gly Pro Gly Lys Gly Arg Glu Ala Val
        35                  40                  45

Ala Asp Val Asn Thr Gly Gly Arg Arg Thr Tyr Tyr Ala Asp Ser Val
    50                  55                  60

Lys Gly Arg Phe Thr Ile Ser Gln Asp Glu Asn Thr Met Tyr Leu Gln
65                  70                  75                  80

Met Asn Asn Leu Lys Pro Glu Asp Thr Ala Thr Tyr Tyr Cys Ala Lys
                85                  90                  95

Gly Arg Cys Ile Ala Val Ala Gly Gly Pro Asp Tyr Trp Gly Gln Gly
            100                 105                 110

Thr Leu Val Thr Val Ser Ser
        115
```

<210> SEQ ID NO 2
<211> LENGTH: 122
<212> TYPE: PRT
<213> ORGANISM: Artificial sequence
<220> FEATURE:
<223> OTHER INFORMATION: Synthetic construct

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Asn Met Gly Trp Phe Arg Arg Ala Pro Gly Lys Glu Arg Glu Phe Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Leu Val Thr Val Ser Ser
        115                 120
```

<210> SEQ ID NO 3
<211> LENGTH: 122
<212> TYPE: PRT
<213> ORGANISM: Artificial sequence
<220> FEATURE:
<223> OTHER INFORMATION: Synthetic construct

```
<400> SEQUENCE: 3

Glu Val Gln Leu Leu Glu Ser Gly Gly Gly Leu Val Gln Pro Gly Gly
1               5                   10                  15

Ser Leu Arg Leu Ser Cys Ala Ala Ser Gly Leu Thr Phe Ser Ser Tyr
            20                  25                  30

Asn Met Gly Trp Val Arg Gln Ala Pro Gly Lys Gly Leu Glu Trp Val
        35                  40                  45

Ala Ser Ile Thr Trp Ser Gly Arg Asp Thr Phe Tyr Ala Asp Ser Val
    50                  55                  60

Lys Gly Arg Phe Thr Ile Ser Arg Asp Asn Ser Lys Asn Thr Leu Tyr
65              70                  75                  80

Leu Gln Met Asn Ser Leu Arg Ala Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Leu Val Thr Val Ser Ser
            115                 120

<210> SEQ ID NO 4
<211> LENGTH: 20
<212> TYPE: PRT
<213> ORGANISM: Artificial sequence
<220> FEATURE:
<223> OTHER INFORMATION: Synthetic construct

<400> SEQUENCE: 4

Met Lys Lys Ile Trp Leu Ala Leu Ala Gly Leu Val Leu Ala Phe Ser
1               5                   10                  15

Ala Ser Ala Ser
            20
```

BISPECIFIC ANTIBODY AND ANTIBODY CONJUGATE FOR TUMOR THERAPY AND USE THEREOF

CROSS-REFERENCE TO RELATED APPLICATIONS

This application is a national phase entry under 35 USC § 371 of International Application PCT/CN2017/089307, filed Jun. 21, 2017, and entitled BISPECIFIC ANTIBODY AND ANTIBODY CONJUGATE FOR TUMOUR THERAPY AND USE THEREOF, which claims priority to and benefits of Chinese Patent Application Nos. 201610456791.8 filed on Jun. 22, 2016, and 201710052692.8 filed on Jan. 24, 2017, the disclosure of which are hereby incorporated in their entireties by this reference.

TECHNICAL FIELD

The present invention relates to a bispecific antibody and the preparation thereof, and more particularly to a bispecific antibody directing to MUC1 and CD16 for use in the field of tumor therapy.

BACKGROUND

In tumor immunotherapy, a bispecific antibody (bsAb) plays a very important role. A bispecific antibody is an artificial antibody containing two specific antigen binding sites. The antibody can simultaneously bind to the specific antigens on the surfaces of an effector cell and a target cell through binding sites, activate quiescent effector cells and recruit them around the target cells and mediate apoptosis or lysis of targeting cells. A variety of bsAbs targeting different immune effector cells and tumor cells have been developed, wherein the main immune effector cells in tumor immunotherapy are T cells, NK cells, macrophages and the like. NK cells and T cells are currently the most studied effector cells.

There are molecules having priming effect on the surface, including CD2, CD3, CD28, and so on. Therefore, when constructing bispecific antibodies for tumor therapy, it usually needs to identify the specificity of these molecules, wherein the bispecific antibodies based on CD3 and CD28 are more researched. BiTE (bispecific T cell recruiter) is a bispecific antibody that maximizes the mediation of T cells to approach tumor cells by single-chain antibody fragment of anti-CD3, thereby lysing tumors. Currently, several targeting BiTEs are under development, such as CD19 (which directs to B cell carcinoma), epithelial cell adhesion molecule (EpCAM, CD326), prostate specific membrane antigen (PSMA), and MUC1. MEDI-565, also known as MT111 or AMG211, is a BiTE antibody that mediates T cell killing of tumor cells expressing MUC1 and is independent of the mutation status of tumor cell lines. The drug is now in clinical phase I trials (ClinicalTrails.gov, NCT02291614) for the treatment of advanced colon adenocarcinoma. Despite these advances, the main challenges of bispecific antibodies remain, such as increased manufacturing efficiency, retention of immunogenicity, reduced toxicity, and increased half-life.

Natural killer (NK) cells are an important part of in vivo immunity, which recognizes external antigens in innate immunity and directly removes them. The killing effect of NK cells is MHC non-limiting, and a variety of tumor cells are sensitive to NK cell-mediated killing. The surface-specific molecule CD16 is a low-affinity Fc receptor distributed on the surface of NK cells, neutrophils and monocytes, macrophages and the like. CD16 activates NK cells to produce ADCC by binding to the Fc region of IgG. The anti-CD16 antibody binding site on the bsAb molecule can increase the NK cell-based immunotherapy effect in two aspects: (1) as an anchoring molecule at the tumor site, recruiting NK cells, increasing the number of local NK cells, prolonging contact time between the tumor cells with NK cells, and enhancing the killing effect of NK cells; (2) activating NK cells at the tumor site, thereby killing tumors. A variety of bispecific antibodies that bind CD16 and tumor-associated antigens have been studied, such as those targeting Her2-related breast cancer, CD33, CD20, and the like. The bispecific antibody AFM13 targeting CD30 and CD16 for the treatment of refractory and/or recurrent Hodgkin's lymphoma has entered clinical trial (clinicaltrials.gov identifier: NCT01221571).

MUC1 is a member of the mucin family (Mucins), which exists on the surface of normal ductal epithelial cells and tumor cells derived therefrom, and is composed of a polypeptide core (core peptide) and a side branch sugar chain. The extracellular segment of the core peptide contains variable numbers (SAPDTRPAPGSTAPPAHGVT) tandem repeats (VNTRs) having 20 amino acids. MUC1 of normal tissue is different from that of tumor tissue. The former is distributed in the secretory duct of glandular epithelial cells, relatively separated from immune cells and rich in glycosylation. The latter is widely distributed, abnormally abundantly expressed on the surface of cancer cells, and has incomplete glycosylation, and thus exposes hidden epitope and becomes a target being attacked by immune cells. The PDTRP epitope of the MUC1 core peptide can be recognized by both various types of MUC1 antibodies and be recognized and killed by CTL cells.

In addition, bispecific antibodies may have poor pharmacokinetic and physical properties (such as immunogenicity) as well as manufacturing difficulties. Therefore, improvements or alternative techniques to such prior art are required.

SUMMARY OF THE INVENTION

The present invention provides a bispecific antibody comprising an anti-MUC1 VHH antibody fragment and an anti-CD16 VHH antibody fragment, wherein the anti-MUC1 VHH antibody fragment has an amino acid sequence as shown in SEQ ID No. 1, and the anti-CD16 VHH antibody fragment has an amino acid sequence as shown in SEQ ID No. 2 or SEQ ID No. 3.

In some embodiments, the anti-MUC1 VHH antibody fragment and the anti-CD16 VHH antibody fragment in the bispecific antibody are connected by a linker peptide.

In some embodiments, the amino acid sequence of the linker peptide is set forth in SEQ ID No. 4.

In some embodiments, the manner of attachment between the anti-MUC1 VHH antibody fragment and the anti-CD16 VHH antibody fragment in the bispecific antibody is: anti-MUC1 VHH-linker peptide-anti-CD16 VHH.

In other embodiments, the manner of attachment between the anti-MUC1 VHH antibody fragment and the anti-CD16 VHH antibody fragment in the bispecific antibody is: anti-CD16 VHH-linker peptide-anti-MUC1 VHH.

Another aspect of the invention provides a pharmaceutical composition comprising a bispecific antibody of the invention and a pharmaceutically acceptable additive comprising a carrier, a stabilizer and/or an excipient.

Another aspect of the invention provides a nucleotide sequence encoding the bispecific antibody of the invention, an expression vector comprising the nucleotide sequence, or a host transformed or transfected with the expression vector.

Another aspect of the present invention also provides a method of treating a subject having cancer, the method comprising administering to a subject in need thereof a therapeutically effective amount of the bispecific antibody of the present invention or a pharmaceutical composition thereof.

Another aspect of the present invention also provides the use of the bispecific antibody of the present invention for the preparation of a medicament for treating cancer.

A further aspect of the invention provides an antibody conjugate comprising a bispecific antibody as described above coupled to a nanomaterial, such as a nanoparticle. The nanoparticle may be a biodegradable nanomaterial, preferably any one of or a mixture of at least two of poly(lactic acid-co-glycolic acid), polylactic acid, polycaprolactone, polybutylene succinate, polyaniline, polycarbonate, poly (glycolide-co-lactide) or poly(glycolide-co-caprolactone), most preferably poly(lactic acid-co-glycolic acid), polylactic acid and/or polycaprolactone.

A further aspect of the invention provides a pharmaceutical composition comprising an antibody conjugate of the invention. The pharmaceutical composition may also comprise a cytotoxic effector cell. Preferably, the cytotoxic effector cell is leukocyte selected from the group consisting of a T cell, NK cell, NKT cell, macrophage, neutrophil, eosinophil, preferably a cytotoxic effector cell selected from the group consisting of a T cell and NK cell. The pharmaceutical composition is preferably used for immunotherapy.

A further aspect of the invention also provides a method of treating a subject having cancer, the method comprising administering to a subject in need thereof a therapeutically effective amount of an antibody conjugate of the invention or a pharmaceutical composition thereof.

A further aspect of the invention also provides the use of an antibody conjugate of the invention in the manufacture of a medicament for the treatment of cancer.

The invention provides an anti-MUC1-CD16 bispecific antibody, which is constructed from the anti-CD16 and anti-MUC1 nanobody fragments in the same antibody molecule, can specifically bind to CD16 and MUC1, and directs NK cells to approach the MUC1-expressing cells which in turns kills tumor or inhibits tumor growth through ADCC effect.

The antibody fragment used in the present invention is a variable region sequence derived from a heavy chain camelid antibody and has high binding affinity to an antigen. According to the invention, the antibody fragments recognizing MUC1 and recognizing CD16 are constructed in the same antibody molecule, which can specifically bind to MUC1 and CD16 molecules, promote the killing effect of NK cells on MUC1-expressing cells, and inhibit the growth of MUC1 positive tumor. The molecule can be expressed in soluble form in a prokaryotic expression system, which facilitates subsequent isolation and purification. The molecule has good thermal stability and high solubility. The nanobody sequence used in the present invention has high homology with the variable heavy chain sequence of the human immunoglobulin and has low antigenicity. Furthermore, the bispecific antibody provided by the present invention has all been humanized.

DRAWINGS

FIG. 1: Schematic representation of the structure of an anti-CD16-MUC1 bispecific nanobody.

Figure 2:
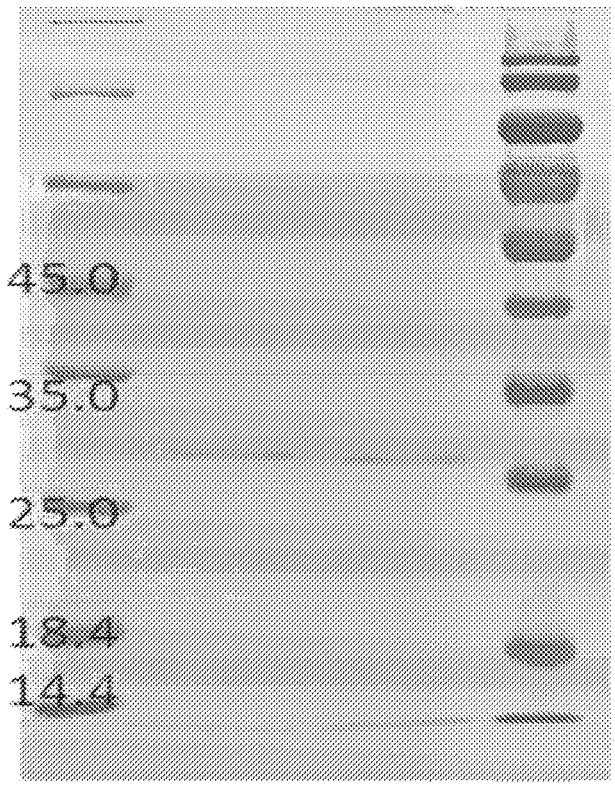

FIG. 2: Electropherogram of purifying anti-MUC1-anti-CD16 antibody.

Figure 3:
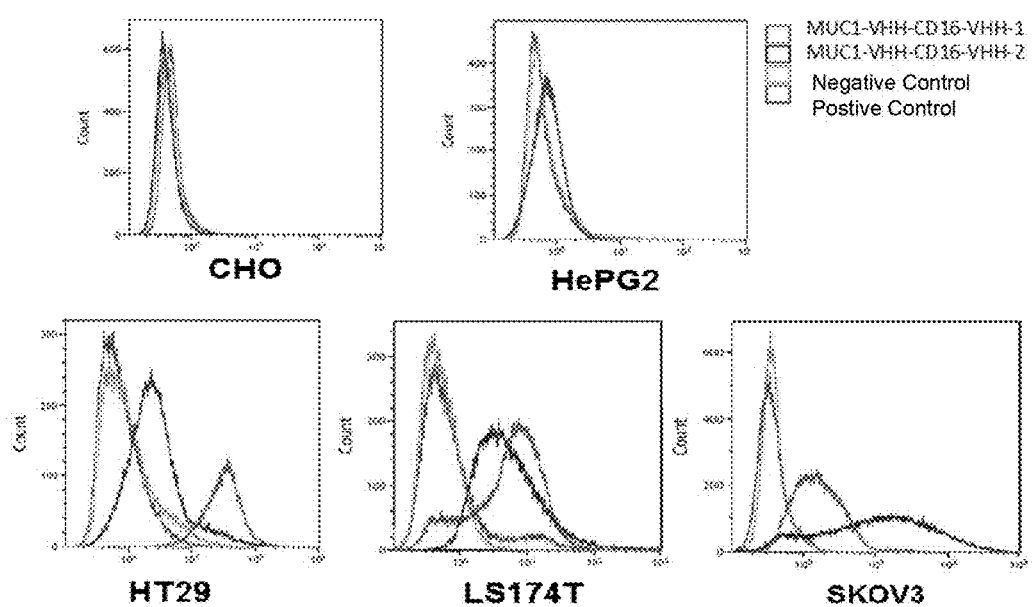

FIG. 3: Flow cytometry detection of bispecific antibodies binding to MUC1 on the surface of tumor cells.

Figure 4:
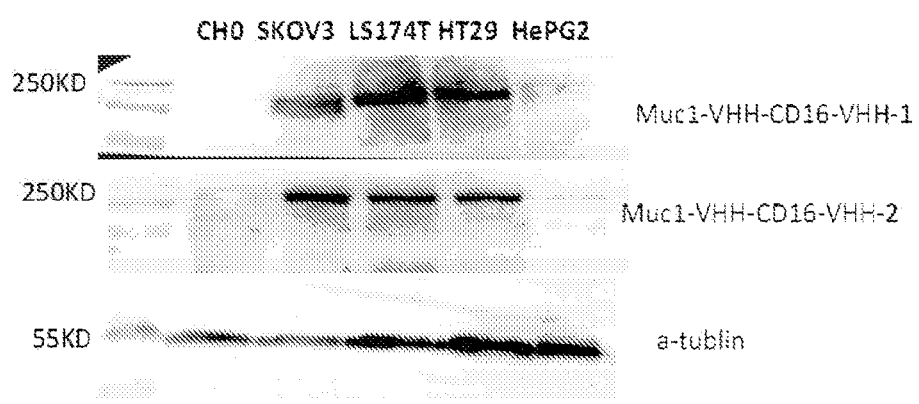

FIG. 4: Western blot analysis of bispecific antibodies specifically binding to MUC1 expressed by cells such as LS174T, HT29 and SKOV3, but not to total protein in CHO and HepG2.

Figure 5:
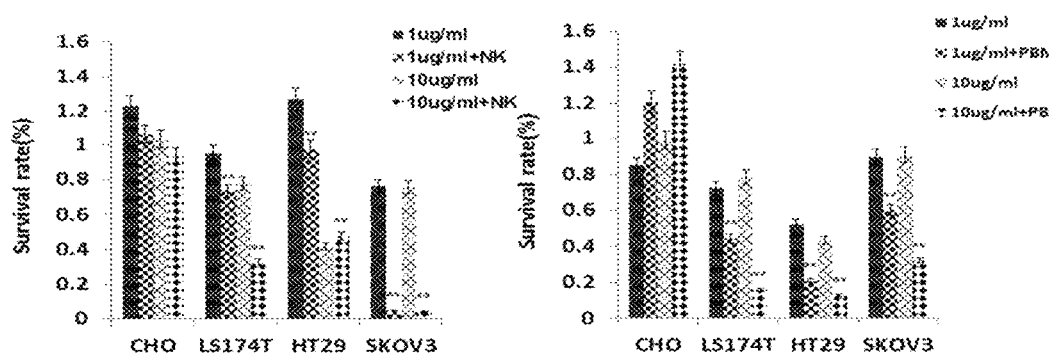

FIG. 5: Muc1-VHH-CD16-VHH-1 (wherein the sequence of Muc1-VHH is shown in SEQ ID NO. 1 and the sequence of CD16-VHH is shown in SEQ ID NO. 2) mediates the killing effect of NK/PBMC cells on tumor cells.

Figure 6:
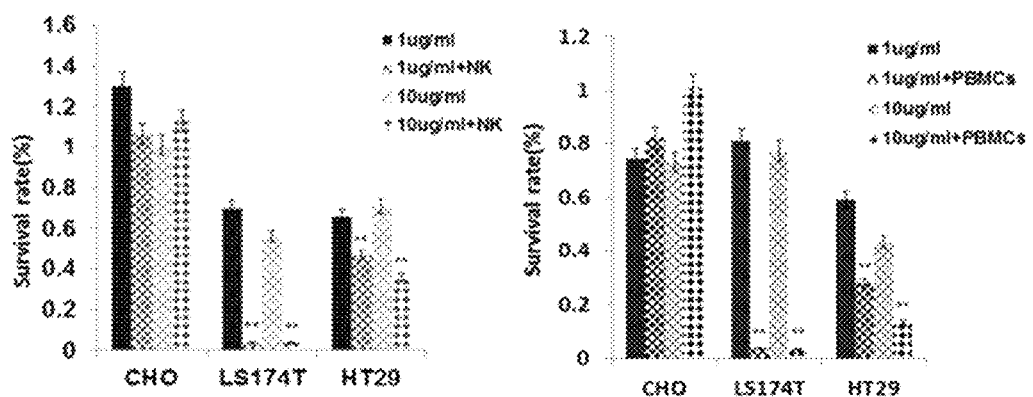

FIG. 6: Muc1-VHH-CD16-VHH-2 (wherein the sequence of Muc1-VHH is shown in SEQ ID NO. 1 and the sequence of CD16-VHH is shown in SEQ ID NO. 3) mediates the killing effect of NK/PBMC cells on tumor cells.

Figure 7:
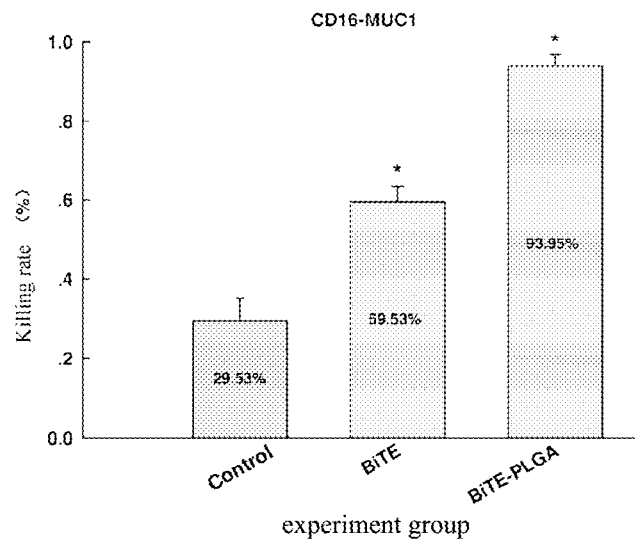

FIG. 7: The killing rate of the bispecific antibody BiTE (CD16-MUC1) and the antibody conjugate BiTE(CD16-MUC1)-PLGA combined with NK cells on lung cancer cells A549 (human non-small cell lung cancer cells) is shown.

Figure 8:
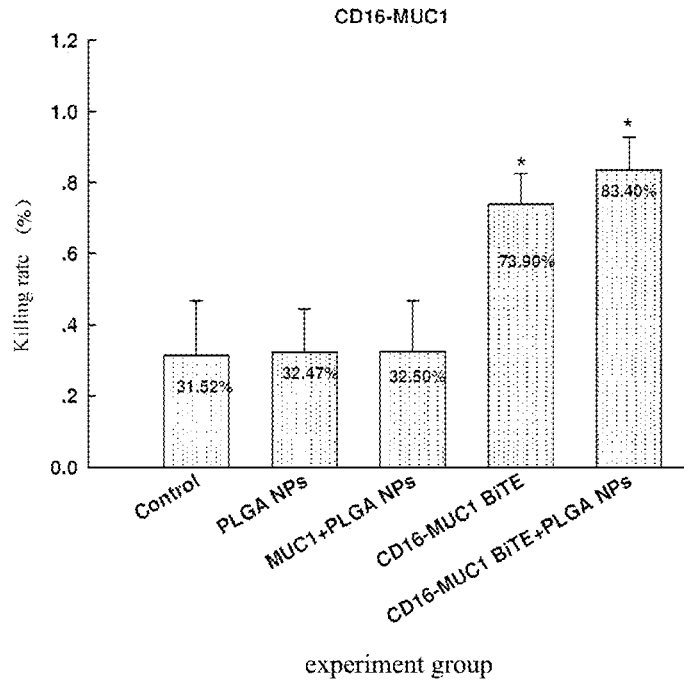

FIG. 8: The killing rate of the bispecific antibody CD16-MUC1 BiTE or the bispecific antibody conjugate CD16-MUC1 BiTE-PLGA NP combined with NK on lung cancer cell A549 (human non-small cell lung cancer cells) is shown, wherein the effector to target ratio is 4:1.

DESCRIPTION

Before describing the antibody, antibody conjugate, method, and composition of present invention, it is to be understood that the invention is not limited to the particular antibody, antibody conjugate, method, or composition described herein, and thus may, of course, vary. It is also understood that the terminology used herein is for the purpose of describing the particular embodiments, but not limiting. The described Examples is provided for a person of ordinary skill in the art to know how to make and use the present invention. It is not intended to limit the scope of the invention, and is not intended to indicate that the performed experiments as follow are the all experiments or the only experiments. Efforts have been made to ensure the accuracy of the numbers used (e.g., amount, temperature, etc.), but some experimental errors and deviations should be considered.

Unless defined otherwise, all technical and scientific terms used herein have the same meaning as commonly understood by one of ordinary skill in the art. Some potential and preferred methods and materials are now described, although any methods and materials similar or equivalent to those described herein can be used in the practice or testing of the present invention. All publications mentioned herein are hereby incorporated by reference to disclose and describe the methods and/or materials related to the cited publication. It will be understood that in the event of a conflict, the disclosure of the subject application controls.

As will be apparent to those skilled in the art upon reading this disclosure, each individual embodiment described and illustrated herein has discrete components and features that can be readily separated or combined with features in several other embodiments. The scope or spirit of the invention is not departed. Any of the enumerated methods can be implemented in the order of the recited events or in any other order that is logically possible.

Definition

It should be noted that the term "a" entity refers to one or more of the entities. For example, "a bivalent antibody" is understood to mean one or more bivalent antibodies. Likewise, the terms "a", "an", "one or more" or "at least one" are used interchangeably.

"Homology", "identity" or "similarity" refers to sequence similarity between two polypeptide sequences or between two nucleic acid molecules. Homology is determined by comparing the positions at each sequence, and each sequence may be aligned for comparison purposes. When the position of the compared sequences is occupied by the same base or amino acid, these molecules are homologous at that position. The degree of homology between sequences varies with the number of matching or homologous positions shared by these sequences. An "unrelated" or "non-homologous" sequence refers to a sequence having less than 40% identity, preferably less than 25% identity to one of the sequences of the invention.

A polynucleotide or polynucleotide region (or polypeptide, polypeptide region) having "sequence identity" to another sequence at certain percentage (e.g. 60%, 60%, 65%, 70%, 75%, 80%, 85%, 90%, 95%, 98% or 99%) means that when aligned, the two compared sequences have identical bases (or amino acids) at the described percentage. The alignment and percentage of homology or sequence identity can be determined by using software programs known in the art.

The term "identical polynucleotide" refers to a nucleic acid sequence that has some degree of homology or sequence identity to a reference nucleic acid sequence or its complement. In one aspect, a homolog of a nucleic acid is capable of hybridizing to the nucleic acid or its complement. Similarly, an "identical polypeptide" refers to a polypeptide that has some degree of homology or sequence identity to the amino acid sequence of a reference polypeptide. In certain aspects, the identity of the sequences is at least about 70%, 75%, 80%, 85%, 90%, 95%, 98%, or 99%. In some aspects, the sequences having such identity maintain the activity (e.g., epitope binding) or structure (e.g., salt bridge) of the reference sequence.

Each of the polypeptides or polynucleotides disclosed herein and the equivalents thereof are also contemplated. In one aspect, an equivalent of a polypeptide includes a modification (i.e., deletion, addition or substitution) of an amino acid residue. In one aspect, an equivalent of a polypeptide comprises no more than two amino acid residue modifications. In one aspect, an equivalent of a polypeptide includes no more than 3, 4 or 5 amino acid residue modifications. In some aspects, such amino acid modifications are located at residues that are not critical to the activity of the reference polypeptide. Residues critical for polypeptide activity can be readily tested by site-specific mutation analysis, or even sequence alignment (because this sequence is highly conserved).

As used herein, "antibody" or "antigen binding polypeptide" refers to a polypeptide or polypeptide complex that specifically recognizes and binds to one or more antigens. An antibody can be a whole antibody or any antigen binding fragment or single chain thereof. Thus, the term "antibody" includes any protein or peptide comprising at least a portion of an immunoglobulin molecule which has biological activity for binding to an antigen. An example includes, but is not limited to, the complementarity determining region (CDR) of the heavy/light chain or its ligand binding portion, the heavy or light chain variable region, the heavy or light chain constant region, the framework (FR) region or any portion thereof, or at least a portion of binding protein. The term antibody also encompasses a polypeptide or polypeptide complex that possesses antigen binding ability upon activation.

The term "antibody fragment" or "antigen-binding fragment" as used herein is part of an antibody, such as F(ab')$_2$, F(ab)$_2$, Fab', Fab, Fv, scFv, and the like. Regardless of the structure, the antibody fragment binds to the same antigen recognized by the intact antibody. The term "antibody fragment" includes an aptamer, spiegelmer, diabody. The term "antibody fragment" also includes any synthetic or genetically engineered protein that acts like an antibody by binding to a specific antigen to form a complex.

An antibody, an antigen binding polypeptide, or a variant or derivative thereof according to the invention includes, but is not limited to, a polyclonal antibody, monoclonal antibody, multispecific antibody, human antibody, humanized antibody, primatized antibody or chimeric antibody, single-chain antibody, epitope-binding fragment (e.g., Fab, Fab' and F(ab')2, Fd, Fvs, single-chain Fvs (scFv)), single-chain antibody, disulfide-linked Fvs (sdFv), fragment comprising a VK or VH domain, fragment generated from a Fab expression library, and anti-Id antibody (including, for example, the anti-Id antibody and LIGHT antibody disclosed herein). The immunoglobulin or antibody molecule of the invention may be an immunoglobulin molecule of any type (e.g., IgG, IgE, IgM, IgD, IgA, and IgY), species (e.g., IgG1, IgG2, IgG3, IgG4, IgA1, and IgA2) or subtype.

The light chain is classified into kappa or lambda (κ, λ). Each heavy chain species can be complexed with a kappa or lambda light chain. In general, the light and heavy chains are covalently bound to each other. When immunoglobulins are produced by hybridoma, B-cell or genetically engineered host cells, the "tails" of the two heavy chains are attached with each other through a covalent disulfide bond or non-covalent bond. In the heavy chain, the amino acid sequence runs from the N-terminus at the forked end of the Y conformation to the C-terminus at the bottom of each chain.

Structural and functional homologous regions are divided in both light and heavy chains. The terms "constant" and "variable" are used functionally. In this regard, it will be understood that both the light chain variable domain (VK) and the heavy chain variable domain (VH) determine antigen recognition and specificity. Conversely, the constant domains of the light chain (CK) and heavy chain (CH1, CH2 or CH3) confer important biological properties such as secretion, transplacental fluidity, Fc receptor binding, complement binding, and the like. By convention, the numbering of the constant region domains increases as they become distant from the antigen binding site or the amino terminus of the antibody. The N-terminal portion is a variable domain and the C-terminal portion is a constant domain; the CH3 and CK domains actually comprise the carboxy terminuses of the light and heavy chains, respectively.

As described above, the variable region allows the antibody to selectively recognize and specifically bind to an epitope on the antigen. In other words, the VK domain and VH domain of an antibody, or a subtype of complementarity determining regions (CDRs), bind with each other to form a variable domain that defines a three-dimensional antigen binding site. This antibody structure forms an antigen binding site that is present at the end of each arm of Y. More specifically, the antigen binding site is determined by three CDRs on each VH and VK chain (ie, CDR-H1, CDR-H2, CDR-H3, CDR-L1, CDR-L2, and CDR-L3). In some instances, for example, with respect to certain immunoglobulin molecules derived from Camelidae or engineered from Camelidae immunoglobulin, they may consist solely of heavy chains without any light chain (see for example Hamers-Casterman et al., *Nature* 363:446-448 (1993)).

In a natural antibody, the six "complementarity determining domains" or "CDRs" present in each antigen binding domain are short, non-contiguous amino acid sequences that are specifically positioned to form an antigen binding domain in a three-dimensional conformation in an aqueous environment. The amino acids of the remaining portion in the antigen binding domain (referred to as the "framework region") exhibit lower intermolecular variability. The framework regions are mainly in a beta-sheet conformation, and the CDRs form loops that link the beta-sheet structure and, and in some cases, form a part of the beta-sheet structure. Thus, the framework regions are used to form scaffolds that position the CDRs in the correct orientation by non-covalent interactions between the strands. The antigen binding domain formed by the aligned CDRs defines a surface complementary to the epitope on the immunoreactive antigen. This complementary surface causes the antibody to bind non-covalently to its cognate epitope. For any variable domain of a heavy or light chain, one of ordinary skill in the art can readily identify these amino acids comprising the CDRs and framework regions, respectively, since they have been precisely defined (see "Sequences of Proteins of Immunological Interest," Kabat, E., et al., USDepartment of Health and Human Services, (1983); and Chothia and Lesk, J. MoI. Biol., 196: 901-917 (1987), which are incorporated by reference in their entirety).

If two or more definitions are used and/or accepted in the art for a term, the definition of the term is intended to include all such meanings unless otherwise indicated. A specific example is the term "complementarity determining region" ("CDR") used to describe non-contiguous antigen binding sites that are found in both the variable regions of a heavy chain polypeptide and a light chain polypeptide. This particular region has been described in Kabat et al., U.S. Dept. of Health and Human Services, "Sequences of Proteins of Immunological Interest" (1983) and Chothia et al., *J. Mol Biol.*: 901-917 (1987), which is incorporated herein by reference. According to the definition of CDRs by Kabat and Chothia, it includes overlapping or subpopulations of amino acid residues when compared to each other. However, the use of any definition of a CDR for an antibody or variable region thereof is considered to be within the scope of the terms defined and used in the present invention. Suitable amino acid residues comprising the CDRs as defined in any of the above cited documents are listed in the table below for comparison. The exact number of residues comprising a particular CDR varies depending on the sequence and size of the CDRs. For the amino acid sequence of variable region of an antibody, one skilled in the art can determine the residues comprising a specific CDR by a conventional method.

Kabat et al. also define a numbering system that is adaptable to the variable domain sequences of any antibody. One of skill in the art can explicitly apply the "Kabat numbering" system to any variable domain sequence without relying on any experimental data beyond the sequence itself. As used herein, "Kabat numbering" refers to the numbering system set forth in: Kabat et al., U.S. Dept. of Health and Human Services, "Sequence of Proteins of Immunological Interest" (1983).

"Specifically binding to" or "specific to" generally refers to the binding of an antibody to an epitope by its antigen binding domain, and such binding requires some complementarity between the antigen binding domain and the epitope. According to this definition, an antibody is described to "specifically bind" to an epitope when it is capable of binding to a particular epitope more rapidly via its antigen binding domain than to a random, unrelated epitope. The term "specificity" is used to quantify the relative affinity of a particular antibody for binding to a particular epitope. For example, for a given epitope, antibody "A" is considered to be more specific than antibody "B", or the binding specificity of antibody "A" to epitope "C" is higher than its binding specificity to epitope "D".

The term "treating" or "treatment" as used herein refers to a therapeutic or prophylactic means in which an undesired pathological change or disorder, such as the progression of cancer, is prevented from or slowed (mitigated) in a subject. Beneficial or desirable clinical outcomes include, but are not limited to, alleviation of symptoms, reduction in disease severity, stabilization of disease states (i.e., no deterioration), delay or slowing of disease progression, improvement or mitigation of disease states, and relief (whether local or holistic, regardless whether or not these results are detectable or undetectable. "Treatment" also refers to prolonged survival as compared to the expected survival without treatment. Subjects in need of treatment include those already having the disease or condition as well as those who are prone to have the disease or condition or who are in need of prevention from the disease or condition.

"Subject" or "individual" or "animal" or "patient" or "mammal" refers to any subject, particularly a mammalian subject, who requires a diagnosis, prognosis or treatment. A mammalian subject includes human, domestic animal, farm animal, and zoo animal, competitive animal, or pet, such as dog, cat, guinea pig, rabbit, rat, mouse, horse, cattle, cow, and the like.

The term "patient in need of treatment" or "subject in need of treatment" includes a subject, such as a mammalian subject, that can benefit from administration of an antibody or composition of the invention to achieve, for example, detection, diagnostic procedures, and/or therapeutic purposes.

The bispecific antibody of the invention also comprises a linker sequence between antibody fragments, which is typically a short peptide of 2-20 amino acids. These linker sequences allow for proper positioning between the components to achieve functional activity of the components.

Preferably, the linker sequence comprises sequences having from 2 to 20 amino acids, more preferably from 5 to 20 amino acids. The linker sequence is preferably a flexible linker sequence such that it does not limit the effector molecule or polypeptide in a single undesired conformation. The linker sequence is preferably composed primarily of amino acids having small side chains, such as glycine, alanine and serine, to provide said flexibility. Preferably, the amino acid in a ratio of about 80% or more in the linker sequence is a glycine, alanine or serine residue, in particular a glycine and a serine residue. An example of a suitable linker sequence is GGGGS ($G_4S$), i.e. Gly Gly Gly Gly Ser; or $(G_4S)_3$. Other different linker sequences can also be used, including a variety of flexible linkers that have been successfully used to link different antibody variable regions. The size and sequence composition of the linker sequence can be determined by conventional computer modeling and techniques.

Any of the antibodies or polypeptides described above may further comprise an additional polypeptide, for example, a signal peptide that directs secretion of the encoded polypeptide, an antibody constant region as described herein, or the other heterologous polypeptide as described herein.

One of ordinary skill in the art will appreciate that the an antibody disclosed herein can be modified such that they differ in amino acid sequence from the native binding polypeptide from which they are derived. For example, polypeptides or amino acid sequences derived from a particular protein may be similar, for example, having a certain identity percentage to the initial sequence. For example, they may have 60%, 70%, 75%, 80%, 85%, 90%, 95%, 98% or 99% identity to the initial sequence.

In addition, a conservative substitution, deletion or addition of nucleotide or amino acid can be made in the "non-essential" amino acid region. For example, a polypeptide or amino acid sequence derived from a particular protein may be identical to the initial sequence except one or more single amino acid substitutions, additions, or deletions (e.g., one, two, three, four, five, six, seven, eight, nine, ten, fifteen, twenty or more individual amino acid substitutions, additions or deletions). In certain embodiments, the polypeptide or amino acid sequence derived from a particular protein has from one to five, one to ten, or one to twenty individual amino acid substitutions, additions or deletions relative to the initial sequence.

In certain embodiments, an antigen binding polypeptide comprises an amino acid sequence or one or more portions that are not normally attached to an antibody. Exemplary modifications are described in detail below. For example, a fragment of the invention may comprise a flexible linker sequence or may be modified to add a functional moiety (e.g., PEG, drug, toxin or marker).

An antibody, variant or derivative thereof of the invention includes a modified derivative, i.e., any type of molecule covalently linked to the antibody, so long as the covalent linkage does not prevent binding of the antibody to the epitope. For example, but not by way of limitation, an antibody may be modified, for example, via glycosylation, acetylation, PEGylation, phosphorylation, amidation, derivation by known protecting or blocking groups, cleavage by protease, attachment to cell ligand or other protein and so on. Any of a number of chemical modifications can be performed by known techniques including, but not limited to, specific chemical cleavage, acetylation, formylation, metabolic synthesis of tunicamycin, and the like. Furthermore, an antibody may comprise one or more atypical amino acids.

In other embodiments, an antigen binding polypeptide of the invention may comprise a conservative amino acid substitution.

In a "conservative amino acid substitution", one amino acid residue is substituted with an amino acid residue having a similar side chain. A family of amino acid residues having a similar side chain have been defined in the art, including a basic side chains (e.g., lysine, arginine, histidine), an acidic side chain (e.g., aspartic acid, glutamic acid), an uncharged polar side chain (e.g. glycine, asparagine, glutamine, serine, threonine, tyrosine, cysteine), a non-polar side chain (e.g. alanine, valine, leucine, isoleucine, proline, phenylalanine, methionine, tryptophan), b-branched side chain (e.g. threonine, valine, isoleucine) and an aromatic side chain (e.g. tyrosine, phenylalanine, tryptophan, histidine). Thus, the non-essential amino acid residue in the immunoglobulin polypeptide is more suitably substituted by other amino acid residues from the same side chain family. In another embodiment, the amino acid chain can be substituted with a structurally similar chain which, however, is from sequentially or compositionally different member of side chain family.

The following table provides non-limiting examples of conservative amino acid substitutions. A similarity score of 0 or higher in the table indicates a conservative substitution at both amino acids.

In some embodiments, an antibody can be bound to a therapeutic agent, prodrug, peptide, protein, enzyme, virus, lipid, biological effect modifier, pharmaceutical agent, or PEG.

These antibodies can be bound or fused to a therapeutic agent, which can include a detectable label (e.g., a radiolabel), an immunomodulator, a hormone, an enzyme, an oligonucleotide, a photot herapeutic or diagnostic agent, a cytotoxicity agent (a drug or toxin), an ultrasound enhancer, a non-radioactive label, and combinations thereof, and other agents known in the art.

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 1 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

An antibody can be detected by labeling the antibody with a chemiluminescence compound. The presence of the chemiluminescent-labeled antigen-binding polypeptide is then determined by detecting the presence of fluorescence (during the course of a chemical reaction). Examples of extremely useful chemiluminescent labeling compounds are luminol, isoluminol, theromatic acridinium ester, imidazole, acridine salt and oxalate.

Polynucleotide Encoding the Antibody and Method for Preparing the Antibody

The invention also provides an isolated polynucleotide or nucleic acid molecule encoding a bispecific antibody, a variant or derivative thereof.

A polynucleotide of the invention may encode all VHH, variants or derivatives thereof on the same polynucleotide molecule or on separate polynucleotide molecules. Furthermore, a polynucleotide of the invention may encode a portion of an antibody or VHH, a variant or derivative thereof, on the same polynucleotide molecule or on separate polynucleotide molecules.

In certain embodiments, the prepared antibody will not cause a deleterious immune response on a subject animal, such as a human. In one embodiment, the antigen binding polypeptide of the invention, variant or derivative thereof, is modified using the techniques known in the art to reduce their immunogenicity. For example, the antibody can be humanized, primatized, deimmunized, or a chimeric antibody can be prepared.

The binding specificity of the bispecific antibodies of the invention can be determined by in vitro assays (e.g., immunoprecipitation, radioimmunoassay (RIA) or immunoenzymatic adsorption (ELISA)).

Production System and Method

The invention also provides a method and system for producing the bispecific antibody of the invention. Cells suitable for the production of antibody known in the art include human cells (e.g., CHO cells), mammalian cells, and bacterial cells. The use of bacterial cells to produce a bispecific antibody presents significant challenges. However, as shown in the examples, when an antibody is expressed in a bacterial cell, the produced antibody is largely soluble even if both peptide chains are expressed in the same cell.

Thus, in one embodiment, the invention provides a host cell comprising one or more polynucleotides encoding two chains of a bispecific antibody of the invention. In one aspect, a single nucleotide construct (e.g., a plasmid) includes two coding sequences. In another aspect, the invention provides two different polynucleotide constructs, each encoding one of the polynucleotide strains. In one embodiment, the invention also provides a host cell comprising two polypeptide chains of a bispecific antibody of the invention.

In some aspects, the host cell is a human cell. In some aspects, the host cell is a mammalian cell. In some aspects, the host cell is a yeast cell. In some aspects, the host cell is a bacterial cell, including a G+ and G− bacterial cell. Representative bacterial cell includes, but is not limited to, *Escherichia coli* and *Salmonella typhimurium*.

In certain aspects, the invention also provides a method of making the bispecific antibody of the invention. In one aspect, the method entails expressing two peptide chains of the antibody in a host cell and extracting the antibody from the cell lysate. Furthermore, the present invention also provides a bispecific antibody obtained by these methods.

The nanomaterial used in the present invention may be a pharmaceutically acceptable nanomaterial, preferably a biodegradable nanomaterial, such as a nanoparticle. More preferably, the nanomaterial is any one of or a mixture of at least two of poly(lactic acid-co-glycolic acid), polylactic acid, polycaprolactone, polybutylene succinate, polyaniline, polycarbonate, poly(glycolide-co-lactide) or poly(glycolide-co-caprolactone), most preferably poly(lactic acid-co-glycolic acid) (PLGA), polylactic acid (PLA) and/or polycaprolactone (PCL). The average particle diameter of the nanoparticle may be, for example, about 10-990 nm, for example, about 900 nm, about 850 nm, about 800 nm, about 750 nm, about 700 nm, about 650 nm, about 600 nm, about 550 nm, about 500 nm, about 450 nm, about 400 nm., about 350 nm, about 300 nm, about 250 nm, about 200 nm, about 150 nm, about 100 nm, or less than 100 nm, such as about 90 nm, about 80 nm, about 70 nm, about 60 nm, about 50 nm, about 40 nm, about 30 nm, about 20 nm, or about 10 nm. Preferably, the nanoparticle has an average particle diameter in the range of 10 to 500 nm, more preferably in the range of 10 to 300 nm, 50 to 250 nm, 80 to 250 nm, 100 to 250 nm or 100 to 200 nm.

Preparation of the Conjugate of the Invention

The method of preparing the bispecific antibody conjugate of the present invention is described below. The preparation method comprises the following steps:

(1) preparing, collecting and activating the nanomaterial;
(2) connecting the nanomaterial obtained in step (1) with a bispecific antibody.

In the step (1), the preparation of the nanomaterial comprises: completely dissolving the nanomaterial with a solvent, stirring, adding water to form a uniform emulsion. The agitation may be carried out at a rotation speed of 500 to 20,000 rpm/min, for example, the rotation speed may be 500 rpm/min, 700 rpm/min, 800 rpm/min, 1000 rpm/min, 1100 rpm/min, 1200 rpm/min, 1300 rpm/min, 1400 rpm/min, 1480 rpm/min, 1500 rpm/min, 2000 rpm/min, 2200 rpm/min, 2500 rpm/min, 3000 rpm/min, 3500 rpm/min, 4000 rpm/min, 4200 rpm/min, 4500 rpm/min, 5000 rpm/min, 5500 rpm/min, 6000 rpm/min, 6500 rpm/min, 7000 rpm/min, 7500 rpm/min, 8000 rpm/min, 8500 rpm/min, 9000 rpm/min, 9500 rpm/min, 10000 rpm/min, 11000 rpm/min, 12000 rpm/min, 13000 rpm/min, 14000 rpm/min, 15000 rpm/min, 16000 rpm/min, 17000 rpm/min, 18000 rpm/min, 19000 rpm/min or 20000 rpm/min. Higher speed can be used if necessary.

Preferably, the nanomaterial is any one of or a mixture of at least two of poly(lactic acid-co-glycolic acid) (PLGA), polylactic acid (PLA), polycaprolactone (PCL), polybutylene succinate, polyaniline, polycarbonate, poly(glycolide-co-lactide) or poly(glycolide-co-caprolactone).

Preferably, the solvent is any one of or a mixture of at least two of acetone, butanone, methanol, ethanol or isopropanol.

Preferably, the collection of the nanomaterial comprises: collecting the prepared nanomaterial by centrifugation, and then washing the nanomaterial by resuspending in deionized water twice. The centrifugation can be carried out at a rotation speed of 8000-15000 rpm/min, for example, the rotation speed can be 8000 rpm/min, 9000 rpm/min, 10000 rpm/min, 11000 rpm/min, 12000 rpm/min, 13000 rpm/min, 14000 rpm/min, 14500 rpm/min., 14800 rpm/min, 15000 rpm/min. Higher speeds can be used if necessary. Nanomaterials (nanoparticles) can be collected or further purified by other methods. The nanoparticles may have an average particle size as described above.

Preferably, the activation of the nanomaterial comprises: activating the nanomaterial for 0.5 to 5 hours by using a mixed solvent of 1 to 10 mg/mL 1-ethyl-(3-dimethylaminopropyl)carbodiimide hydrochloride (EDS) and N-hydroxysuccinimide (NHS) at room temperature.

In the step (2) of the invention, the connection comprises: collecting the activated nanomaterial by centrifugation, and then washing the nanomaterial once with the connecting reaction solution. The bispecific antibody to be connected is added into the connecting reaction solution, and then the nanomaterial is suspended with the connecting reaction solution containing the bispecific antibody and the connecting reaction is conducted for 0.5 to 5 hours at room temperature. After the reaction, the nanomaterial is collected by centrifugation. The nanomaterial is washed twice in Dulbecco's phosphate buffer saline (D-PBS), and then resuspended in D-PBS and stored at 4° C. Other methods of activating the nanomaterial can be used.

The method for preparing the bispecific antibody conjugate of the present invention specifically includes the following steps:

(1) preparing a nanomaterial: completely dissolving the nanomaterial in acetone at a concentration of 5 to 30 mg/mL, and adding the solution of the nanomaterial in acetone to the deionized water in 1:4 v/v of acetone and deionized water with magnetic stirring at 500 to 1500 rpm/min, to form a uniform emulsion, and then continuing to stir until the volatilization of acetone;

(2) collecting the nanomaterial: collecting the prepared nanomaterial by centrifugation at 8000 to 15000 rpm/min, and then resuspending in deionized water, which processes are repeated twice for washing the nanomaterial; the nanomaterial can be further purified to obtain nanomaterial with suitable size;

(3) activating the nanomaterial: activating the nanomaterial by using a mixed solvent of 1 to 10 mg/mL 1-ethyl-(3-dimethylaminopropyl)carbodiimide hydrochloride and N-hydroxysuccinimide at room temperature for 0.5 to 5 hours;

(4) connecting the nanomaterial with antibodies: collecting the activated nanomaterial by centrifugation, and then washing the nanomaterial once with 0.1 M D-PBS at pH=8.0, and adding the bispecific antibody to be connected into the connecting reaction solution, and then resuspending the nanomaterial with the connecting reaction solution containing the bispecific antibody to be connected and conducting the connecting reaction for 0.5 to 5 hours at room temperature. After the reaction, the nanomaterial is collected by centrifugation. The nanomaterial is washed twice in D-PBS, and then resuspended in D-PBS and stored at 4° C.

Therapeutic and Diagnostic Methods

As noted above, the bispecific antibody, variant or derivative thereof of the invention are useful in certain therapeutic and diagnostic methods associated with cancer or infectious diseases.

The invention further relates to an antibody-based therapy which involves administering a bispecific antibody of the invention to a patient, such as an animal, a mammal and a human, to treat one or more of the diseases or conditions described herein. Therapeutic composition of the invention includes, but is not limited to, an antibody of the invention (including a variant and derivative thereof described herein) and a nucleic acid or polynucleotide encoding an antibody of the invention (including a variant and derivative thereof described herein).

The antibody of the invention can be used to treat, inhibit or prevent a disease, disorder, or condition, including a malignant disease, disorder, or condition associated with, for example, a disease or disorder (such as cancer) associated with increased cell survival or inhibited apoptosis. The cancer includes, but is not limited to, follicular lymphoma, cancer with p53 mutation, and hormone-dependent tumor (including but not limited to colon cancer, cardiac tumor, pancreatic cancer, melanoma, retinal neoplasia, glioblastoma, lung cancer, colorectal cancer, testicular cancer, gastric cancer, neuroblastoma, myxoma, fibroid, lymphoma, endothelial tumor, osteoblastoma, osteoclast, osteosarcoma, chondrosarcoma, adenocarcinoma, breast cancer, prostate cancer, Kaposi sarcoma); autoimmune disorder (e.g. multiple sclerosis, Sjogren syndrome, Grave disease, Hashimoto thyroiditis, autoimmune diabetes, biliary cirrhosis, Behcet's disease, Crohn's disease, polymyositis, systemic lupus erythematosus, immune-related glomerulonephritis, autoimmune gastritis, autoimmune thrombocytopenic purpura and rheumatoid arthritis); and viral infection (such as herpes virus, pox virus and adenovirus, inflammation, graft versus host disease (acute and/or chronic), acute graft rejection, and chronic graft rejection. The antigen binding polypeptide, variant or derivative thereof of the invention is used to inhibit the development, progression and/or metastasis of cancer, particularly the cancers listed above or in subsequent paragraphs.

The antibody or the variant or derivative thereof according to present invention can be used for treatment, prevention, and diagnosis and/or prognosis of other diseases or conditions that may be associated with increased cell viability, including, but not limited to, progression and/or metastasis of the following diseases: malignancy and related diseases such as leukemia (acute leukemia (such as acute lymphocytic leukemia, acute myeloid leukemia (including myeloblast, promyelocytic leukemia, myelomonocyte, monocyte, and leukemia cell)) and chronic leukemia (such as chronic myeloid (granulocyte) leukemia and chronic lymphocytic leukemia), erythrocytosis, lymphoma (such as Hodgkin's disease and non-Hodgkin's disease), multiple myeloma, Waldenstrom macroglobulinemia, heavy chain disease, and solid tumor (including but not limited to: sarcoma and cancer (such as fibrosarcoma, mucinous sarcoma, liposarcoma, chondrosarcoma, osteogenic sarcoma, spinal tumor, angiosarcoma, endothelial sarcoma, lymphosarcoma, lymphatic endothelial sarcoma, synovial tumor, mesothelium tumor, Ewing tumor, leiomyoma, rhabdomyosarcoma, colon cancer, pancreatic cancer, thymic carcinoma, ovarian cancer, prostate cancer, squamous cell carcinoma, basal cell carcinoma, adenocarcinoma, syringocarcinoma, papillary carcinoma, papillary adenocarcinoma, cystadenocarcinoma, medullary carcinoma, bronchial carcinoma, renal cell carcinoma, liver cancer, cholangiocarcinoma, choriocarcinoma, seminoma, embryogenic cancer, Wilm tumor, cervical cancer, testicular tumor, lung cancer, small cell lung cancer, bladder cancer, epithelial cancer, glioma, squamous cell tumor, medulloblastoma, craniopharyngioma, ependymoma, pineal gland tumor, hemangioblastoma, acoustic neuroma, mesenchymal glioma, meningioma, melanoma, neuroblastoma, and ocular cell membrane tumor)).

The antibody of the present invention can also be used to treat infectious diseases caused by microorganisms or to kill microorganisms by targeting microorganisms and immune cells to affect the elimination of microorganisms. In one aspect, the microorganism is a virus (including RNA and DNA viruses), a Gram-positive bacterium, a Gram-negative bacterium, a protozoa or a fungus.

The dosage and treatment regimen specific for any particular patient will depend on a variety of factors (including an specific antigen binding polypeptide used, a variant or derivative thereof, an antibody conjugate, the age of patient, weight, overall health, gender, diet, administration time, excretion rate, combination of drugs, and severity of the particular disease being treated). The judgment of the medical staff on such factors is within the judgment of those of ordinary skill in the art. The dosage will also be based on the individual patient being treated, the route of administration, the type of formulation, the characteristics of the composition used, the severity of the disease, and the desired effect. The dosage used can be determined by the principles of pharmacology and pharmacokinetics well known in the art.

Methods of administration of the bispecific antibody, variant, antibody conjugate include, but are not limited to, intradermal, intramuscular, intraperitoneal, intravenous, subcutaneous, intranasal, epidural, and oral routes. The antigen binding polypeptide or composition can be administered by any convenient route, for example, by infusion or bolus injection, by absorption of the epithelial or mucosal protective layer (e.g., oral mucosa, rectal and intestinal mucosa, etc.); and used with other biologically active agents. Thus, a pharmaceutical composition comprising an antigen binding polypeptide of the invention may be administered orally, rectally, parenterally, intravaginally, intraperitoneally, topically (e.g., by powder, ointment, drop or dermal patche), buccally, or via spray application to the oral cavity or nose.

The term "parenteral" as used herein refers to the manner of administration, including intravenous, intramuscular, intraperitoneal, intrasternal, subcutaneous, and intra-articular injection and infusion.

Administration can be systemic or topical. Furthermore, it is contemplated that the antibody of the invention can be introduced into the central nervous system by any suitable route, including: intraventricular and intrathecal injection. Intraventricular injection can be achieved by intraventricular catheters (e.g., attachment to a reservoir (e.g., Ommaya reservoir)). Pulmonary administration can also be used, for example, by using an inhaler or nebulizer and a formulation with an aerosol.

It may be desirable to topically administer a bispecific antibody, antibody conjugate or composition of the invention to a region in need of treatment. This may be accomplished, for example, but not limited to, by local infusion during surgery, topical administration (for example, in combination with a wound dressing after surgery), injection, through a catheter, through a suppository, or through an implant (the implant is a porous, non-porous, non-permeable or gel-like material, including a film (e.g., a silicone membrane)) or fiber)). Preferably, when a protein (including an antibody) according to the present invention is administered, care should be taken to use a material that the protein does not adsorb.

An effective amount of an antibody, antibody conjugate of the invention in the treatment, inhibition and prevention of an inflammatory, immune or malignant disease, disorder or condition can be determined by standard clinical techniques. In addition, in vitro assays can be optionally used to help identifying the optimal dose range. The exact dose to be used in the formulation will also depend on the route of administration and the severity of the disease, disorder, or condition, and should be determined in accordance with the judgment of the practitioner and the condition of each patient. Effective doses can be deduced from dose-response curve derived from in vitro or animal model test systems.

As a general recommendation, the dose of the antigen-binding polypeptide of the present invention administered to a patient is usually from 0.1 mg/kg to 100 mg/kg of patient body weight, from 0.1 mg/kg to 20 mg/kg of patient body weight, or from 1 mg/kg to 10 mg/kg of patient body weight. In general, human antibodies have a longer half-life in human than antibodies from other species due to the immune response to exogenous polypeptides. Therefore, lower doses and lower dosing frequency of human antibodies are generally possible. Moreover, the frequency and dosage of administration of the antibodies of the invention can be reduced by modification (e.g., lipidation) to enhance the uptake of these antibodies and tissue penetration (e.g., into the brain).

The dosage of the conjugate administered to a human will vary depending on factors such as the age, weight, height, sex, general medical condition, and past medical history of the patient. It may be desirable to provide the subject with a conjugate dose as a single intravenous infusion in the range of about 0.1 µg/kg to 25 mg/kg (in the first binding portion and the second binding portion in the multispecific antibody conjugate). However, lower or higher doses can also be administered, as the case may be. For example, for a 70 kg patient, a dose of 0.1 µg/kg to 20 mg/kg is 0.7 µg to 1400 mg. The dose can be repeated as needed, for example, once a week for 4-10 weeks, once a week for 8 weeks or once a week for 4 weeks. In maintenance therapy, it can also be administered at a lower frequency, if desired, such as every other week for several months, or monthly or quarterly for many months. It is also possible to administer 2, 3, 4, 5 or 6 times continuously for each course of treatment, for example, at an interval of about 10 days, 15 days, 20 days, 25 days, 30 days, 35 days, 40 days, 45 days, 50, 55 days or 60 days or more after continuous administration for the next course of treatment.

The conjugate can be administered with effector cells such as leukocytes (NK cells), for example, via intravenous reinfusion. The conjugate is administered with effector cells, for example, once a week for 4-10 weeks, once weekly for 8 weeks, or once weekly for 4 weeks. In maintenance therapy, the conjugate and effector cells can also be administered at a lower frequency, for example once a week or every few weeks for several months, or monthly or quarterly for many months. It is also possible to administer 2, 3, 4, 5 or 6 times continuously for each course of treatment, for example, at an interval of about 10 days, 15 days, 20 days, 25 days, 30 days, 35 days, 40 days, 45 days, 50, 55 days or 60 days or more after continuous administration for the next course of treatment.

A method for treating an infectious or a malignant disease, disorder or disorder, (comprising administering an antibody, variant or derivative thereof, antibody conjugate of the present invention) is usually tested in vitro prior to use in a human body, and then is tested in vivo in animal models to obtain the desired therapeutic or prophylactic activity. Suitable animal models, including transgenic animals, are well known to those of ordinary skill in the art. For example, in vitro assays demonstrating the therapeutic utility of the antigen binding polypeptides described herein include the effect of antigen binding polypeptides on cell lines or patient tissue samples. The effect of an antigen binding polypeptide on a cell lines and/or tissue samples can be determined using techniques known to those of skill in the art, such as those disclosed elsewhere herein. In vitro assays that can be used to determine whether a specific antigen-binding polypeptide is required for use in accordance with the present invention include in vitro cell culture assays (where patient tissue samples are grown in culture medium and exposed or otherwise administered to the antibody) and the effect of antibodies on this tissue sample is observed.

In a further embodiment, the compositions of the invention are administered in combination with an anti-neoplastic, antiviral, antibacterial or antibiotic or antifungal agent. Any of these agents known in the art can be administered in the compositions of the present invention.

In another embodiment, the compositions of the invention are administered in combination with a chemotherapeutic agent. Chemotherapeutic agents that can be administered with the compositions of the present invention include, but are not limited to, antibiotic derivatives (e.g., doxorubicin, bleomycin, daunorubicin, actinomycin), antiestrogens (e.g., tamoxifen)), antimetabolites (e.g., fluorouracil, 5-FU, methotrexate, fluorouridine, interferon a-2b, glutamic acid, pucamycin, guanidine, and 6-mercaptoguanine), cytotoxic agents (e.g., carmustine, BCNU, lomustine, CCNU, cytarabine, cyclophosphamide, estramustine, hydroxyurea, benzamidine, mitomycin, busulfan, cisplatin and vincristine sulfate), hormone (e.g. medroxyprogesterone, estramustine sodium phosphate, ethinyl estradiol, estradiol, megestrol acetate, metotestosterone, diethylstilbestrol, ketene estradiol and testosterone), nitrogen mustard derivatives (phenylalanine mustard, chlorambucil, dichloromethyldiethylamine (nitrogen mustard), thiotepa), steroids and products (betamethasone sodium phosphate) and others (e.g. dacarbazine, asparaginase, mitoxantrone, vincristine sulfide, vinblastine sulfide and etoposide).

In additional embodiments, the compositions of the invention are administered in combination with a cytokine. Cytokines that can be administered with the compositions of the invention include, but are not limited to, IL-2, IL-3, IL-4, IL-5, IL-6, IL-7, IL-10, IL-12, IL-13, IL-15, anti-CD40, CD40L and TNF-a.

In additional embodiments, the compositions of the invention are administered in combination with other therapeutic or prophylactic therapies, such as radiation therapy.
Composition The invention also provides pharmaceutical compositions. Such compositions comprise an effective amount of an antibody and/or antibody conjugate and an acceptable carrier. In a specific embodiment, the term "pharmaceutically acceptable" means approved by a federal or state government regulatory agency, or listed in the US Pharmacopoeia or other generally recognized pharmacopoeia for use in animals, and more specifically for use in human. Further, a "pharmaceutically acceptable carrier" will generally be a non-toxic solid, semi-solid or liquid filler, diluent, encapsulating material or any type of excipient.

The term "carrier" refers to a diluent, adjuvant, excipient or carrier with which the drug is used. Such pharmaceutical carriers may be sterile liquid such as water and oils including oils of petroleum, animal, vegetable or synthetic origin, such as peanut oil, soybean oil, mineral oil, sesame oil and the like. Water is the preferred carrier when the pharmaceutical composition is administered intravenously. Salt solution or aqueous dextrose or glycerol solution can also be used as a carrier for the liquid phase, especially for injectable solution. Suitable pharmaceutical excipient include: starch, glucose, lactose, sucrose, gelatin, malt, rice, flour, chalk, silica gel, sodium stearate, glyceryl monostearate, talc, sodium chloride, skim milk powder, glycerol, propylene, ethylene glycol, water, ethanol, and the like. If desired, the compositions may also contain minor amounts of wetting or emulsifying agents or pH buffering agents such as, for example, acetate, citrate or phosphate. It is also contemplated to add an antibacterial agent (such as benzyl alcohol or methyl benzoate); an antioxidant (such as ascorbic acid or sodium bisulfate); a chelating agent (ethylenediaminetetraacetic acid) and an agent for isotonicity adjustment (such as sodium chloride or dextrose). These compositions may take the form of a solution, suspension, tablet, pill, capsule, powder, sustained release formulation and the like. The composition can be formulated as a suppository using conventional binders and carriers such as triglycerides. Oral formulations may include standard carriers such as pharmaceutical grades of mannitol, lactose, starch, magnesium stearate, sodium saccharin, cellulose, magnesium carbonate, and the like. Examples of suitable pharmaceutical carriers are described by Re. E. W. Martin in Remington's Pharmaceutical Sciences (which is incorporated herein by reference). Such compositions will contain a therapeutically effective amount of the antigen binding polypeptide (preferably in a purified form) with a suitable amount of carrier to provide a suitable mode of administration for the patient. This formulation should be suitable for the mode of administration. Such parental preparations can be enclosed in ampoules, disposable syringes or multi-dose vials made of glass or plastic.

In one embodiment, the composition is formulated according to routine procedures as a pharmaceutical composition suitable for intravenous administration to humans. Typically, the composition for intravenous administration is a solution in sterile isotonic aqueous buffer. The composition may also include a solubilizing agent and a local anesthetic (e.g., lidocaine to reduce pain at the injection site), if necessary. The components are usually provided, either alone or in combination, in unit dosage form, for example, as a lyophilized powder or a water-free concentrate in a closed container, such as an ampoule or sachette indicating the amount of active agent. When the composition is administered by infusion, it can be dispersed in an infusion bottle containing sterile pharmaceutical grade water or saline. When the composition is administered by injection, an ampoule of sterile water or saline for injection can be provided so that the ingredients can be mixed prior to administration.

The compositions of the invention may be formulated in a neutral or salt form. Pharmaceutically acceptable salts include those formed from anions such as those derived from hydrochloric acid, phosphoric acid, acetic acid, oxalic acid, tartaric acid, and the like, and salts formed from cations such as those derived from sodium, potassium, ammonium, calcium, and hydrogen. a salt of iron oxide, isopropylamine, triethylamine, ethylhydroxyethylamine, histidine, procaine or the like.

Example 1—Design and Synthesis of Anti-CD16-MUC1 Bispecific Nanobody Nucleotide Sequences Based on the sequence and ligation format of the bispecific antibody, the nucleotide sequence was redesigned and optimized, and a NcoI restriction site was added at the 5' end, and a Hind III restriction site was added at the 3' end of the sequence. DsbA-anti-MUC1VHH-GS-anti-CD16VHH-6His was directly synthesized and ligated into the vector pETDuet™ by double digestion to form an expression plasmid. A schematic diagram of the structure of the anti-CD16-MUC1 bispecific nanobody is shown in FIG. 1.

Example 2—Vector Transformation of BL21 (DE3)

The plasmid was transformed into *Escherichia coli* DH5a competent cell line, positive clones were selected, cultured in LB medium (3 mL) containing 100 μg/ml ampicillin at 37° C. overnight, the culture solution was centrifuged at 5000 rpm and the supernatant was discarded. The plasmids were extracted from *E. coli* by using plasmid extraction kit from Qiagen and the expression vector was obtained.

Example 3—Expression and Purification of Anti-MUC1-Anti-CD16

The purified pETDuet™-bsAb expression vector was transformed into *E. coli* BL21 (DE3) strain, and positive clones were selected and cultured in LB medium (3 mL) containing 100 μg/mL ampicillin overnight at 37° C., and then transferred to 300 mL LB containing 100 μg/mL ampicillin, and the cells were cultured at 37° C. until the OD600 was at 0.6-0.8. IPTG was added at a final concentration of 0.05 mM, and the culture was induced at 16° C. for 16 hours. The culture was centrifuged at 4000 rpm, and the supernatant was discarded. The precipitate was added to a solution of 20 mM Tris-HCl, pH 8.0, 25% sucrose, 1 mM EDTA in a weight-to-volume ratio of 1:4, resuspended, ice-bathed for 30 min, and centrifuged at 4° C., 8500 g, for 20 minutes. The supernatant was taken. The precipitate was added at a weight ratio of 1:5 to solution containing 5 mM $MgCl_2$ and 1 mg/mL lysozyme, ice-cooled for 20 min, and centrifuged at 4° C., 8500 g, for 20 minutes. The supernatant was taken.

Binding:

The two supernatants were combined and passed through a 2 mL Ni-NTA (Qiagen) gravity settling column.

Removal:

The impurities were removed by using 20 mL 20 mM Tris-HCl pH 8.0, 15 mM imidazole, 1 M NaCl and 20 mL 20 mM Tris-HCl pH 8.0, 25 mM imidazole, 1 M NaCl, sequentially.

Elution:

Elution was conducted by using 10 mL 20 mM Tris-HCl pH 8.0, 50 mM imidazole, 0.15 M NaCl, 10 mL 20 mM Tris-HCl pH 8.0, 100 mM imidazole, 0.15 M NaCl, 10 mL 20 mM Tris-HCl pH 8.0, 200 mM imidazole, 0.15M NaCl, 10 mL 20 mM Tris-HCl pH 8.0, 500 mM imidazole, 0.15 M NaCl, sequentially.

The fractions eluted with 50 mM imidazole, 100 mM imidazole and 200 mM imidazole were combined, dialyzed with 20 mM PB, pH 7.6, 10% glycerol at 4° C. overnight.

1 mL Q-HP Purification:

After dialysis overnight, the solution containing target component was centrifuged at 20,000 g, at 4° C. for 20 min, and the sample was loaded at a flow rate of 1 mL/min, and the flow-through components were collected for ultrafiltration concentration.

The experimental results are shown in FIG. 2.

Example 4—Bispecific Antibody In Vitro Binding to MUC1 Test

Method:
1). Flow Cytometry Detects the Binding of Bispecific Antibody to MUC1
1. MUC1 positive cells LS174T, HT29, SKOV3 and negative cells CHO, HepG2 cells were cultured in vitro; 0.25% trypsin was digested into single cells, and after centrifugation at 1000 rpm for 10 min, the cell pellet was collected and resuspended in ice-cold PBS+0.2% BSA.
2. Centrifuged at 4° C., 1000 rpm, for 5 minutes, discarded the supernatant
3. Resuspend in ice-cold PBS+0.2% BSA and configured to a cell suspension with a concentration of $2*10^6$/mL.
4. The primary antibodies (mouse anti-MUC1/CD66e mAb (1:200); bsAb (10 ug/mL)) were added separately as per the following table and then were incubated for 1 hour at 4° C.

| Tube number | Primary antibodies | Secondary antibodies |
|---|---|---|
| A | None | Goat-Anti-mouse IgG-FITC (1:500) |
| B | Anti-MUC1 (1:200) | Goat-Anti-mouse IgG-FITC (1:500) |
| C | None | Anti-His-FITC (1:500) |
| D | bsAb (10 ug/mL) | Anti-His-FITC (1:500) |

5. Added 5 mL ice-cold PBS+0.2% BSA;
6. Centrifugated at 1000 rpm, 4° C. for 5 minutes;
7. The cell pellet was resuspended in ice-cold 1 mL PBS+0.2% BSA;
8. Centrifuged at 1000 rpm, 4° C. for 5 minutes;
9. The cell pellet was resuspended in 0.5 mL ice-cold PBS+0.2% BSA;
10. Added the secondary antibodies as per the above table, and incubated at 4° C. for 1 hour;
11. Centrifuged at 1000 rpm, 4° C. for 5 minutes;
12. The cell pellet was resuspended in ice-cold 1 mL PBS+0.2% BSA;
13. Centrifuged at 1000 rpm, 4° C. for 5 minutes;
14. The cell pellet was resuspended in 1 mL of ice-cold PBS+0.2% BSA;
15. Centrifuged at 1000 rpm, 4° C. for 5 minutes;
16. The cell pellet was resuspended in 1 mL of ice-cold PBS+0.2% BSA and tested on a machine.

Experimental Results:

bsAb can bind to MUC1 on the surface of tumor cells, and the results are shown in FIG. 3.

2). Western Blot Detection of Bispecific Antibody Binding to MUC1

MUC1 positive cells LS174T, HT29, SKOV3 and negative cells CHO, HepG2 cells were cultured in vitro, and the protein content was determined by BCA method after RIPA lysis.

SDS-PAGE Electrophoresis:

The concentration of separation gel was 8%. The lysate loading of each cell line was 30 μg, a constant pressure at 120 V was applied for 45 minutes, and then the membrane was transferred.

Transfer of Film:

After SDS-PAGE electrophoresis, the separation gel was placed on the negative electrode, the PVDF film was placed on the positive electrode, and wet transfer was carried out at, 100V for 90 minutes.

Blocking:

The transferred PVDF membrane was placed in TBST containing 5% skim milk powder, and blocked for 1 hour;

Primary Antibody Incubation:

Bispecific antibody (1 mg/mL) was diluted at 1:1000 in TBST containing 5% skim milk powder and incubated for 1 hour at room temperature; commercial anti-MUC1 rabbit monoclonal antibody (Abcam, article number:) was used as positive control, diluted at 1:1000, and incubated for 1 hour. Rabbit anti-GAPDH monoclonal antibody was used as internal reference (Abcam, article number:)

Washing the Membrane:
TBST was washed three times, 10 minutes each time;
Secondary Antibody Incubation:
Anti-His IgG-HRP was diluted in TBST at a ratio of 1:3000 and incubated for 1 hour at room temperature; the positive control secondary antibody was incubated with anti-rabbit IgG HRP at a dilution of 1:5000 for 1 hour.
Washing the Membrane:
TBST was washed three times, 10 minutes each time;
Color Development:
The film was placed in chemiluminescence imaging system of to Biorad, and the millipore color developer was evenly added, and the development was photographed in the dark.
Experimental Results:
The bispecific antibody specifically binds to MUC1 expressed by the cells such as LS174T, HT29 and SKOV3, but does not bind to total protein in CHO and HepG2. The results are shown in FIG. 4.

Example 5—In Vitro Cytotoxicity Assay

1. In Vitro Cytotoxicity Test
1) SKOV3, HT29 and LS174T tumor cells were digested with 0.25% trypsin to form a single cell, and then plated into 96-well plates at 5000 cells per well and incubated at 37° C., 5% carbon dioxide for 6 hours.
2) $5*10^4$ NK cells were added to each well, and bsAb were added at 0 μg/mL, 0.28 μg/mL, and 2.8 μg/mL, respectively, and incubated at 37° C., 5% carbon dioxide for 48 hours.
3) Aspirated the medium and gently washed twice with PBS.
4) Added CCK8 reagent and incubated for 2 hours
5) The OD450 reading was measured using a microplate reader with a reference of 620 nm.
6) The lysis rate was calculated by the following formula:
The lysis rate=1−(As−Ab)/(A0−Ab), where Ab is the absorption value of blank control, As is the absorption value of experimental group, and A0 is the absorption value of the well without any drug.
The experimental results are shown in FIGS. 5 and 6.

2. EC50 Test
1) After LS174T tumor cells were digested with 0.25% trypsin into individual cells, 96-well plates were plated with 5000 cells per well and incubated at 37° C., 5% carbon dioxide for 6 hours.
2) $5*10^4$ NK cells were added to each well, and bsAb were added at 0 μg/mL, 0.28 μg/mL, and 2.8 μg/mL, respectively, and incubated at 37° C., 5% carbon dioxide for 48 hours.
3) Aspirated the medium and gently washed twice with PBS.
4) Added CCK8 reagent and incubated for 2 hours
5) The OD450 reading was measured using a microplate reader with a reference of 620 nm.
6) The lysis rate was calculated by the following formula:
The lysis rate=1−(As−Ab)/(A0−Ab), where Ab is the absorption value of blank control, As is the absorption value of experimental group, and A0 is the absorption value of the well without any drug.

| bispecific nanobody | $EC_{50}$ |
| --- | --- |
| Muc1-VHH-CD16-VHH-1 | 0.16 uM |
| Muc1-VHH-CD16-VHH-2 | 0.08 uM |

Example 6. Preparation of Bispecific Antibody Conjugate

A bispecific antibody conjugate (BiTE (CD16-MUC1)-PLGA) having a bispecific antibody CD16-MUC1 BiTE coupled to PLGA nanoparticles, respectively, was prepared. The "CD16-MUC1 BiTE" is a bispecific antibody wherein a Muc1 VHH having sequence shown in SEQ ID NO: 1 and CD16 VHH-2 having sequence shown in SEQ ID NO: 3 were conjugated by a linker peptide having the sequence shown in SEQ ID NO: 3.
The preparation method of the bispecific antibody conjugate is as follows:
(1) Preparation of PLGA Nanoparticles:
PLGA was completely dissolved in acetone to a concentration of 5 mg/mL; and a solution of PLGA and acetone was added to deionized water by stirring at 1000 rpm/min in a volume ratio of acetone and deionized water of 1:4 to form a uniform emulsion, which then was continued to be stirred until the acetone was evaporated;
(2) Collection of PLGA Nanoparticles:
The prepared nanoparticles with larger particle size were collected by centrifugation at 8000 rpm/min for 10 min; and the nanoparticles with smaller particle size were collected by centrifugation at 15,000 rpm/min for 10 min. The larger nanoparticles were discarded, the smaller nanoparticles were resuspended in deionized water, and the nanoparticles were washed twice in duplicate. The nanomaterial can be further purified to obtain smaller nanoparticles. The nanoparticles with smaller particle size were used to perform the following operations;
(3) Activation of PLGA Nanoparticles:
PLGA nanoparticles were activated with a mixed solvent of 5 mg/mL 1-ethyl-(3-dimethylaminopropyl)carbodiimide hydrochloride and N-hydroxysuccinimide at room temperature for 1 h;
(4) Connection of Antibody with PLGA Nanoparticles:
The activated nanomaterial was collected by centrifugation, and then the nanomaterial was washed once with 0.1 M, pH=8.0 Dulbecco's phosphate buffer solution. BiTE (CD16-MUC1) or BiTE (CD16-CEA) to be connected was added to the solution of connection reaction, and then the nanomaterial was resuspended with the solution of connection reaction containing the BiTE, and the reaction was allowed to proceed at room temperature for 0.5 h. After the reaction, the nanomaterials were collected by centrifugation, and the nanomaterials were washed twice with Dulbecco's phosphate buffer solution, and then resuspended in Dulbecco's phosphate buffer solution and stored at 4° C.

Example 7. Effect of the Bispecific Antibody Conjugate on Killing Cancer Cells

The ability of the bispecific antibody conjugate prepared in Example 6 to kill tumor cells was evaluated.
Specifically, 5,000 target cells/well were cultured in a 96-well plate for 12 hours, and the original medium was discarded. The cytokine-free X-vivo 15™ medium (purchased from Lonza) was used to adjust the density of NK cells (obtained by inducing and amplifying peripheral blood mononuclear cells from healthy blood donors) so that the number of NK cells in a volume of 100 μl was 4 times that of the target cells (The effector-target ratio is 4:1). 100 μl of NK cell suspension was added to the culture plate of cancer cell, and 10 μl of the prepared bispecific antibody conjugate (0.2 mg of bispecific antibody conjugate content, containing 0.2 μg BiTE) or bispecific antibody (BiTE (CD16-MUC1))

(0.2 µg) was added, and incubated in the incubator for 8 h. Then CCK-8 reagent was added and incubation was conducted according to the reagent instruction. The absorbance was detected with the microplate reader at 450 nm. The data was statistically analyzed and the killing rate of DC-CIK cells on cancer cells was calculated according to the following formula.

Killing rate=[1−(experimental group−effector control group)/(target control group−blank control group)]×100%

The blank control indicates the addition of the medium; the target control group indicates the addition of the target cells+medium; the effector control group indicates the addition of the effector cells+medium; the experimental group indicates the addition of the effector cells+target cells+medium+bispecific antibody conjugate.

The results are shown in Table 1 and FIG. 7. FIG. 7 shows the killing rate of the bispecific antibody BiTE (CD16-MUC1) and the antibody conjugate BiTE (CD16-MUC1)-PLGA in combination with NK cells on lung cancer cells A549 (human non-small cell lung cancer cells). The control means addition of effector cells+target cells+medium; BiTE means addition of effector cells+target cells+medium+BiTE; BiTE-PLGA means addition of effector cells+target cells+medium+BiTE-PLGA (i.e., the bispecific antibody conjugate) wherein the PLGA nanoparticles have an average particle size of about 50 nm.

TABLE 1

Ability of bispecific antibody and bispecific antibody conjugate to kill tumor cells (effector-target ratio of 4:1)

| | | Killing rate | |
|---|---|---|---|
| | | | Experimental group |
| Cancer cells | Effector control group (NK) | BiTE (CD16-MUC1) | BiTE (CD16-MUC1)-PLGA |
| A549 | 29.53% | 59.53% | 93.95% |

Example 8

A bispecific antibody conjugate having a PLGA nanoparticle with average particle size of about 100-150 nm was prepared according to the method of Example 6 using the same bispecific antibody. In addition, the conjugate of Muc1 VHH (the sequence of which is shown in SEQ ID NO: 1) prepared by using the same PLGA nanoparticles was used as a control.

The ability of the prepared bispecific antibody conjugate to kill tumor cells was evaluated.

Specifically, 5,000 target cells/well were cultured in a 96-well plate for 12 hours, and the original medium was discarded. The cytokine-free X-vivo 15™ medium (purchased from Lonza) was used to adjust the density of NK cells (obtained by inducing and amplifying peripheral blood mononuclear cells from healthy blood donors) so that the number of NK cells in a volume of 100 µl was 4 times that of the target cells (the effector-target ratio is 4:1). 100 µl of NK cell suspension was added to the culture plate of cancer cell, and 10 µl of the prepared bispecific antibody conjugate CD16-MUC1 BiTE+PLGA NPs (0.2 mg of conjugate content, containing 0.2 µg CD16-MUC1 BiTE) or bispecific antibody (BiTE) (0.2 µg) was added, or Muc1+PLGA NPs (0.2 mg of conjugate content, containing 0.1 ng Muc1 VHH) or PLGA nanoparticles (i.e., PLGA NPs) (0.2 mg) was added as a control, and incubated in the incubator for 48 h. Then CCK-8 reagent was added and incubation was conducted according to the reagent instructions. The absorbance was measured with at 450 nm a microplate reader. The data was statistically analyzed, and the killing rate of DC-CIK cells on cancer cells was calculated according to the following formula.

Killing rate=[1−(experimental group−effector control group)/(target control group−blank control group)]×100%

The blank control indicates the addition of the medium; the target control group indicates the addition of the target cells+medium; the effector control group indicates the addition of the effector cells+medium; the experimental group indicates the addition of the effector cells+target cells+medium+bispecific antibody conjugate.

The results are shown in Table 2 and FIG. 8. Table 2 and FIG. 8 show the killing rate of the bispecific antibody BiTE and the antibody conjugate BiTE-PLGA in combination with NK cells on lung cancer cells A549 (human non-small cell lung cancer cells). Control means addition of effector cells+target cells+medium; MUC1+PLGA NPs means addition of effector cells+target cells+medium+PLGA nanoparticles; BiTE means addition of effector cells+target cells+medium+bispecific antibody; BiTE-PLGA NPs means addition of effector cells+target cells+medium+bispecific antibody conjugate.

TABLE 2

Ability of bispecific antibody or bispecific antibody conjugate to kill tumor cell A549 (effector-target ratio of 4:1)

| Experimental groups | Killing rate |
|---|---|
| control | 31.52% |
| PLGA nanoparticles (PLGA NPs) | 32.47% |
| MUC1 + PLGA NPs | 32.50% |
| CD16-MUC1BiTE | 73.90% |
| CD16-MUC1BiTE + PLGA NPs | 83.40% |

Those skilled in the art will readily appreciate that the present invention can be readily adapted to obtain the objects and advantages described herein as well as those objects and advantages herein. The methods, variations and compositions described herein in the form of the presently preferred embodiments are exemplary and are not intended to limit the scope of the invention. It will be apparent to those skilled in the art that changes may be made thereto or used for other purposes, but are intended to be included within the scope of the invention as defined by the appended claims.

While the invention has been described in terms of the preferred embodiments and the features of the invention, those skilled in the art can make modifications and variations to the concept of the disclosure herein and these modifications and variations fall within the scope of present invention.

The invention claimed is:

1. A bispecific antibody comprising an anti-MUC1 antibody fragment having the amino acid sequence set forth in SEQ ID NO:1 and an anti-CD16 antibody fragment having the amino acid sequence set forth in SEQ ID NO:2 or 3.

2. The bispecific antibody according to claim 1, wherein the anti-MUC1 antibody fragment and the anti-CD16 antibody fragment are connected via a linker peptide.

3. The bispecific antibody according to claim 2, wherein the amino acid sequence of the linker peptide is set forth in SEQ ID NO:4 sequence.

4. The bispecific antibody according to claim 2, having the following structure: anti-MUC1 antibody fragment-linker peptide-anti-CD16 antibody fragment.

5. The bispecific antibody according to claim 2, having the following structure: anti-CD16 antibody fragment-linker peptide-anti-MUC1 antibody fragment.

6. A pharmaceutical composition comprising the bispecific antibody of claim 1 and a pharmaceutically acceptable excipient.

7. A nucleotide sequence encoding the bispecific antibody of claim 1.

8. An expression vector comprising the nucleotide sequence of claim 7.

9. A host cell transformed or transfected with the expression vector of claim 8.

10. A method for treating cancer, comprising administering to a patient in need thereof the bispecific antibody of claim 1.

11. An antibody conjugate comprising the bispecific antibody of claim 1 coupled to a nanoparticle.

12. The antibody conjugate of claim 11, wherein the nanoparticle comprises a biodegradable nanomaterial.

13. The antibody conjugate of claim 12, wherein the biodegradable nanomaterial comprises any one or a mixture of at least two selected from the group consisting of poly (lactic acid-co-glycolic acid), polylactic acid, polycaprolactone, polybutylene succinate, polyaniline, polycarbonate, poly(glycolide-co-lactide), and poly(glycolide-co-caprolactone).

14. The antibody conjugate of claim 13, wherein the biodegradable nanomaterial comprises any one or a mixture of at least two selected from the group consisting of poly (lactic acid-co-glycolic acid), polylactic acid, and polycaprolactone.

15. A pharmaceutical composition comprising the antibody conjugate of claim 11.

16. The pharmaceutical composition according to claim 15, further comprising leukocytes.

17. The pharmaceutical composition according to claim 16, wherein the leukocytes comprise NK cells.

* * * * *